(12) United States Patent
Karagianni

(10) Patent No.: US 11,779,533 B2
(45) Date of Patent: Oct. 10, 2023

(54) HAIR REPAIR COMPOSITION

(71) Applicant: RHODIA OPERATIONS, Paris (FR)

(72) Inventor: Katerina Karagianni, Paris (FR)

(73) Assignee: RHODIA OPERATIONS, Lyons (FR)

( * ) Notice: Subject to any disclaimer, the term of this patent is extended or adjusted under 35 U.S.C. 154(b) by 781 days.

(21) Appl. No.: 16/338,739

(22) PCT Filed: Oct. 3, 2017

(86) PCT No.: PCT/EP2017/075082
§ 371 (c)(1),
(2) Date: Apr. 2, 2019

(87) PCT Pub. No.: WO2018/065416
PCT Pub. Date: Apr. 12, 2018

(65) Prior Publication Data
US 2021/0283040 A1  Sep. 16, 2021

(30) Foreign Application Priority Data
Oct. 4, 2016 (EP) .................................... 16192197

(51) Int. Cl.
*A61Q 5/00* (2006.01)
*A61K 8/73* (2006.01)

(52) U.S. Cl.
CPC .............. *A61K 8/737* (2013.01); *A61Q 5/002* (2013.01); *A61K 2800/5426* (2013.01); *A61K 2800/805* (2013.01)

(58) Field of Classification Search
None
See application file for complete search history.

(56) References Cited

U.S. PATENT DOCUMENTS

| | | | |
|---|---|---|---|
| 3,472,840 A | 10/1969 | Stone et al. | |
| 4,031,307 A | 6/1977 | DeMartino et al. | |
| 4,663,159 A | 5/1987 | Brode, II et al. | |
| 4,959,464 A | 9/1990 | Yeh | |
| 5,387,675 A | 2/1995 | Yeh | |
| 5,473,059 A | 12/1995 | Yeh | |
| 5,756,720 A | 5/1998 | Chowdhary | |
| 6,258,348 B1 * | 7/2001 | Tsivkin | A61P 43/00 424/70.28 |
| 6,475,474 B1 | 11/2002 | Ricca | |
| 8,980,239 B2 | 3/2015 | Staudigel et al. | |
| 2005/0089494 A1 | 4/2005 | Rigoletto, Jr. | |
| 2006/0134047 A1 | 6/2006 | Bakeev et al. | |
| 2006/0251603 A1 | 11/2006 | Rigoletto, Jr. et al. | |
| 2007/0258918 A1 | 11/2007 | Modi | |
| 2010/0029929 A1 | 2/2010 | Luczak et al. | |
| 2011/0213139 A1 | 9/2011 | Chan et al. | |
| 2014/0079659 A1 | 3/2014 | Bendejacq et al. | |
| 2014/0154200 A1 | 6/2014 | Lizarraga et al. | |
| 2014/0308227 A1 * | 10/2014 | Mabille | A61K 8/922 424/70.13 |
| 2015/0183979 A1 * | 7/2015 | Pabalan | C11D 3/3765 525/218 |
| 2015/0313834 A1 | 11/2015 | Hilvert et al. | |

FOREIGN PATENT DOCUMENTS

| | | |
|---|---|---|
| EP | 0511652 A1 | 4/1992 |
| EP | 1552807 A1 | 7/2005 |
| JP | 2003160446 A | 6/2003 |
| JP | 2009286752 A | 12/2009 |
| WO | 2010118925 A2 | 10/2010 |

OTHER PUBLICATIONS

Machine Translation for JP2003160446.
Machine Translation for JP2009286752.
Anonymous, "Deep Recovery Hair Conditioner", in Database MINTEL GNPD [Online], database accession No. 1955609 MINTEL; Dec. 2012.

* cited by examiner

*Primary Examiner* — Jyothsna A Venkat
(74) *Attorney, Agent, or Firm* — Osha Bergman Watanabe & Burton LLP

(57) ABSTRACT

The invention relates to a method for mending split ends of hair comprising contacting the hair with split ends with a composition comprising at least one non-cellulosic polysaccharide derivative containing at least one cationic group, wherein said non-cellulosic polysaccharide derivative has a cationic degree of substitution DScat greater than 0.15.

2 Claims, No Drawings

HAIR REPAIR COMPOSITION

This application claims priority to European application No. 16192197.8, filed on Oct. 4, 2016, the whole content of this application being incorporated herein by reference for all purposes.

The present invention relates to hair care compositions for mending split ends, and more particularly to the use of a specific non-cellulosic polysaccharide derivative as an agent for mending split ends.

Hair is a keratinous substance, which is repeatedly subjected to various stresses including especially environmental factors (such as exposure to UV radiation), damaging treatments (such as bleaching, coloring, perming or thermal straightening), and mechanical stressing, in particular during grooming procedures (for example by frequent brushing, back-combing or combing against high combing resistance).

It results in different types of structural damage to the hair: the cuticles are lifted, and the individual hair fibers may tend to become porous, to snarl, kink and/or interlock with each other.

Impact on the hair texture is noticeable for instance by a poor wet and dry combability, an increased electrostatic charge, increased brittleness, reduced maximum tear force and elongation at break of the hair and/or split ends, so that the hair as a whole looks unhealthy (dull, lifeless, . . . ), is hard to comb and/or feel coarse.

Among these damages, it is an object of the present invention to address the ever increasing demand in the market for hair care compositions which are useful for mending split ends.

The aim of the present invention is therefore to provide an ingredient which is useful for mending split ends.

"Split ends" refers to a condition wherein the ends of the hair are split into two or more shafts.

More especially it is defined as a longitudinal splitting of the hair fiber which develops after the protective cuticle has been stripped away from the end of the hair fibers as a result of either physical or chemical damaging of the hair. Split ends mainly form due to mechanical stresses during grooming routines and especially due to excessive combing forces.

Lubricating agents are already known to prevent or minimize formation of split ends. The lubrication reduces the friction in the hair during combing and hence reduces the strength of the abrasive forces to which the hair is being subjected. This is turn reduces the number of entanglements during the combing process.

The present invention, however, does not seek to prevent split end damages.

The present invention is concerned with split end mending, that is to say repair of existing damage by depositing substances that will restore axial cohesion to splits or "fill in" areas of shaft damage.

It is thus an object of the present invention to provide an ingredient which is effective in mending (i.e. repairing) split ends.

It is also an object of the present invention to provide an ingredient which is additionally effective in repairing hair cuticle damage and/or in aligning the hair fibers.

Repairing hair cuticle damage in the sense of the invention means smoothing hair cuticle. Visual effect may be observed for instance by looking at the hair fiber through scanning electron microscopy.

US 2005/0089494 and US 2006/0251603 disclose that the combination of polyquaternium-28 and methylvinylether/maleic acid copolymer, at particular ratios, produces a polyelectrolyte complex useful to repair split ends.

However, the stability of such polyelectrolyte complexes may be compromised when other ingredients are added to the hair care formulation. In particular, it has been reported that charged compounds and polymers could disrupt the structure of such polyelectrolyte complexes.

U.S. Pat. No. 6,258,348 discloses split-end mending compositions comprising three polymers: guar, a betaine-based polyurethane surfactant, and a silicone polyurethane. As demonstrated in EP1552807 the amphoteric or cationic guar gums disclosed in U.S. Pat. No. 6,258,348 do not achieve substantial split end repair in the absence of the other disclosed polymeric substituents.

The Applicant has now discovered unexpectedly that a specific non-cellulosic polysaccharide derivative is useful as an agent for mending split ends.

There has been no suggestion in the prior art that the specific non-cellulosic polysaccharide derivative of the invention, used alone, would make it possible to achieve substantial split end mending.

The subject of the invention is thus a method for mending split ends of hair comprising contacting the hair with split ends with a composition comprising at least one non-cellulosic polysaccharide derivative containing at least one cationic group, wherein said non-cellulosic polysaccharide derivative has a cationic degree of substitution DScat greater than 0.15.

The present invention is also directed toward a hair care composition for mending split ends comprising at least one non-cellulosic polysaccharide derivative containing at least one cationic group, wherein said non-cellulosic polysaccharide derivative has a cationic degree of substitution DScat greater than 0.15.

The present invention also relates to the use of one non-cellulosic polysaccharide derivative containing at least one cationic group, wherein said non-cellulosic polysaccharide derivative has a cationic degree of substitution DScat greater than 0.15, as an agent for mending split ends.

The present invention also relates to a method of mending split ends of hair comprising applying to the hair with split ends a composition comprising one non-cellulosic polysaccharide derivative containing at least one cationic group, wherein said non-cellulosic polysaccharide derivative has a cationic degree of substitution DScat greater than 0.15.

It has been found that the specific non-cellulosic polysaccharide derivatives of the invention not only provide a high percentage of split end mending, but are also able to close the split ends and to smooth the lifted cuticle scales so as to ensure a durable mend especially after combing or other stress factors during for example hair styling.

Advantageously, the non-cellulosic polysaccharide derivatives of the invention also provide split end mending and hair cuticle repair, without dry hair negatives such as the greasy appearance or feel, sticky feel, loss of gloss and/or heavy, coated feel that many consumers experience when conventional cationic polymers with high charge density and high molecular weight are used.

Should the disclosure of any patents, patent applications, and publications which are incorporated herein by reference conflict with the description of the present application to the extent that it may render a term unclear, the present description shall take precedence.

Non-Cellulosic Polysaccharide Derivative

According to anyone of the invention embodiments, the non-cellulosic polysaccharide derivative of the invention is a galactomannan derivative.

Galactomannans are polysaccharides composed principally of galactose and mannose units, wherein the mannose units are linked in a 1-4-b-glycosidic linkage and the galactose branching takes place by means of a 1-6 a-linkage to mannose units. Each ring of the galactose or mannose units (or sugar units) bears three free hydroxyl groups that are available for chemical reaction. The galactomannans are usually found in the endosperm of leguminous seeds such as guar, locust bean, honey locust, flame tree, and the like.

According to anyone of the invention embodiments, the non-cellulosic polysaccharide starting material used in the present invention is a galactomannan, such as a guar gum, also known as guar.

According to one of the invention embodiments, the non-cellulosic polysaccharide derivative is a guar derivative.

It may be for example a galactomannan that has been modified by chemical means, e.g. quaternization, with one or more derivatizing agents containing reactive groups.

The non-cellulosic polysaccharide derivatives may be obtained for instance by reaction between the hydroxyl groups of the galactomannan and the reactive functional groups of the derivatizing agents.

Methods for the preparation of the non-cellulosic polysaccharide derivative are disclosed in U.S. Pat. Nos. 4,663,159; 5,473,059; 5,387,675; 3,472,840; 4,031,307; 4,959,464 and US 2010/0029929, all of which are incorporated herein by reference.

The non-cellulosic polysaccharide derivative of the invention contains at least one cationic group.

It may also be referred to as a cationic non-cellulosic polysaccharide derivative of the invention.

As used herein, the term "cationic" covers not only positively charged groups, but also groups which may become positively charged depending on the pH.

A cationic non-cellulosic polysaccharide derivative of the invention is a non-cellulosic polysaccharide that has been chemically modified to provide said polysaccharide with a net permanent positive charge in a pH neutral aqueous medium. Those that are non permanently charged, e.g. non-cellulosic polysaccharide derivatives that can be cationic below a given pH and neutral above that pH also fall within the scope of the present invention.

According to anyone of the invention embodiments, the terms "cationizing agents", "cationic groups" and "cationic moieties" include ammoniums (which have a positive charge) but also primary, secondary and tertiary amines and their precursors (which can lead to positively charged compounds).

According to the invention, the non-cellulosic polysaccharide is derivatized or modified so as to contain a cationic group. The resulting compound is the non-cellulosic polysaccharide derivative.

According to one of the invention embodiments, the non-cellulosic polysaccharide derivatives of the invention result from the reaction of any galactomannans, for instance a guar, with a cationizing agent.

Cationizing agents of the present invention are defined as compounds which, by reaction with the hydroxyl groups of the non-cellulosic polysaccharide can lead to a non-cellulosic polysaccharide derivative comprising at least one cationic group according to the invention.

Cationizing agents of the present invention are defined as compounds which contain at least one cationic moiety. Cationizing agents comprise agents which can lead to cationic modified non-cellulosic polysaccharide.

A group of suitable derivatizing reagents typically contain a reactive functional group, such as an epoxy group, a halide group, an ester group, an anhydride group or an ethylenically unsaturated group, and at least one cationic moiety or a precursor of such cationic moiety.

As used herein, the term "derivatizing agent" means an agent containing at least a cationic moiety which is grafted to a non-cellulosic polysaccharide. The term "derivatizing agent" encompasses the terms "cationizing agent" and "grafting agent".

In one embodiment of the invention, the cationic moieties may be linked to the reactive functional group of the derivatizing agent by a bivalent linking group, such as an alkylene or oxyalkylene group. Suitable cationic moieties include primary, secondary, or tertiary amino groups or quaternary ammonium, sulfonium, or phosphinium groups.

The derivatizing agent can comprise a cationic moiety, or a precursor of a cationic moiety, that contains a cationic nitrogen moiety, more typically, a quaternary ammonium moiety. Typical quaternary ammonium moieties are trialkylammonium moieties, such as trimethylammonium moieties, triethylammonium moieties, or tributylammonium moieties, aryldialkylammonium moieties, such as benzyldimethylammonium moieties, and ammonium moieties in which the nitrogen atom is a member of a ring structure, such as pyridinium moieties and imidazoline moieties, each in combination with a counterion, typically a chloride, bromide, or iodide counterion.

According to one of the invention embodiments, examples of cationizing agents, which lead to cationic non-cellulosic polysaccharide derivatives of the invention are:
  cationic epoxides, such as 2,3-epoxypropyltrimethylammonium chloride, 2,3-epoxypropyltrimethylammonium bromide, 2,3-epoxypropyltrimethylammonium iodide;
  chlorohydrin-functional cationic nitrogen compounds, such as 3-halogeno-2-hydroxypropyl trimethylammonium chloride, for example 3-chloro-2-hydroxypropyl trimethylammonium chloride, cationic ethylenically unsaturated monomers or their precursors, such as trimethylammoniumpropyl methacrylamide chloride salt, trimethylammoniumpropyl methacrylamide methylsulfate salt, diallyl dimethyl ammonium chloride, vinyl benzyl trimethylammonium chloride, dimethylaminopropyl methacrylamide (tertiary amine) precursors of cationic monomers, such as N-vinyl formamide, N-vinylacetamide (whose units can be hydrolyzed after polymerization or grafted onto vinyl amine units).

In one embodiment of the invention, the cationizing agents, which lead to cationic non-cellulosic polysaccharide derivatives of the invention are cationic epoxides, such as 2,3-epoxypropyltrimethylammonium chloride, 2,3-epoxypropyltrimethylammonium bromide and 2,3-epoxypropyltrimethylammonium iodide.

According to the invention, the cationic groups may be introduced into a non-cellulosic polysaccharide by reacting the non-cellulosic polysaccharide starting material with a derivatizing agent which comprises a reactive functional group and at least one cationic moiety (or a precursor of cationic moiety).

According to the invention, the cationic groups present in the non-cellulosic polysaccharide derivative are incorporated into the non-cellulosic polysaccharide starting material by reaction of the hydroxyl groups of said polysaccharide with a cationizing agent.

Preferred cationic groups are chosen from the group consisting of: primary, secondary or tertiary amino groups, quaternary ammonium, sulfonium or phosphinium groups, and mixtures thereof. In a particular preferred embodiment, the cationic group is chosen from trialkylammonium groups, such as trimethylammonium groups, triethylammonium groups, tributylammonium groups, aryldialkylammonium groups, such as benzyldimethylammonium groups, and ammonium groups in which the nitrogen atom is a member of a ring structure, such as pyridinium groups and imidazoline groups, each in combination with a counterion, typically a chloride, bromide, or iodide counterion. Preferably, each cationic group contains at least one cationic charge.

The cationicity of the non-cellulosic polysaccharide derivative can be expressed in terms of degree of substitution.

As used herein, the expression "cationic degree of substitution" (DScat) means the average number of moles of cationic groups per mole of sugar unit. The (DScat) may be measured by means of 1H-NMR (solvent:D2O).

Once the 1H NMR spectrum is obtained, the integration of the multiplet of peaks corresponding to the anomeric proton on all guar units, usually between 3.2-4.3 ppm, is normalized to unity. The peak of interest, the one corresponding to the methyl protons of the quaternary ammonium group on guar units, is centered around 1.8 ppm. This peak is integrated for 9 protons given that there are 3 methyl groups on the ammonium function. Therefore the calculation of the (DScationic) for the case of the cationizing agent 2,3-epoxypropyltrimethylammonium chloride is as follows:

$$DS = \frac{INTEGRAL\_N(Me)3}{INTEGRAL\_anomeric\_proton} / 9$$

According to anyone of the invention embodiments, the non-cellulosic polysaccharide derivative of the invention has a cationic degree of substitution (DScat) higher than or equal to about 0.16, for instance higher than or equal to about 0.17, for instance higher than or equal to about 0.18.

According to anyone of the invention embodiments, the non-cellulosic polysaccharide derivative of the invention has a cationic degree of substitution (DScat) lower than or equal to about 0.40, for instance lower than or equal to about 0.35, for instance lower than or equal to about 0.30.

According to one of the invention embodiments, the non-cellulosic polysaccharide derivative of the invention has a cationic degree of substitution (DScat) comprised between about 0.16 and about 0.40, for instance between about 0.17 and about 0.35, for instance between about 0.18 and about 0.30.

The cationicity of the non-cellulosic polysaccharide derivative of the invention may also be expressed in terms of charge density. The cationic degree of substitution may be converted to a charge density through several methods.

The preferred method for calculating charge density of cationic non-cellulosic polysaccharide derivatives uses a method that specifically quantifies the equivalents of quaternary ammonium groups on said polysaccharide.

For cationic guars obtained by reacting a guar gum with 3-chloro-2-hydroxypropyltrimethylammonium chloride or 2,3-epoxypropyltrimethylammonium chloride, the cationic charge density may be calculated from the cationic degree of substitution using the following equation:

Cationic charge density in mequivalents per gram $$(meq/g) = \frac{DS_{cat}}{162 + 151 \times DS_{cat}} \times 1000$$

In general, the equation above depends on the group which is grafted to the non-cellulosic polysaccharide.

As used herein, the term "charge density" refers to the ratio of positive charges on a monomeric unit of which a polymer is comprised to the molecular weight of said monomeric unit. The charge density multiplied by the polymer molecular weight determines the number of positively charged sites on a given polymer chain.

According to the present invention, the non-cellulosic polysaccharide derivative has a charge density from about 0.95 to about 2.00 meq/g, for instance from about 1.0 to about 1.5 meq/g.

By the expression "average molecular weight" of the non-cellulosic polysaccharide derivative of the invention, it is meant the weight average molecular mass of said polysaccharide derivative.

The average molecular weight of a non-cellulosic polysaccharide derivative may be measured by SEC-MALS (Size Exclusion Chromatography with detection by Multi-Angle Light-Scattering detection). A value of 0.140 for dn/dc is used for the molecular weight measurements. A Wyatt MALS detector is calibrated using a 22.5 KDa polyethylene glycol standard. All calculations of the molecular weight distributions are performed using Wyatt's ASTRA software. The samples are prepared as 0.05% solutions in the mobile phase (100 mM Na2NO3, 200 ppm NaN3, 20 ppm pDADMAC) and filtered through 0.45 μm PVDF filters before analysis. The average molecular weights are expressed by weight.

According to anyone of the invention embodiments, the average molecular weight of the non-cellulosic polysaccharide derivative of the invention is higher than about 150,000 g/mol, for instance higher than about 200,000 g/mol, for instance higher than about 250,000 g/mol.

According to anyone of the invention embodiments, the average molecular weight of the non-cellulosic polysaccharide derivative of the invention is lower than about 3,000,000 g/mol, for instance lower than about 2,500,000 g/mol, for instance lower than about 2,000,000 g/mol.

According to one of the invention embodiments, the average molecular weight of the non-cellulosic polysaccharide derivative of the invention is comprised between about 150,000 g/mol and about 3,000,000 g/mol, for instance between about 200,000 g/mol and about 2,500,000 g/mol, for instance between about 250,000 g/mol and 2,000,000 g/mol.

According to one of the invention embodiments, the average molecular weight of the non-cellulosic polysaccharide derivative of the invention is comprised between about 150,000 g/mol and about 1,000,000 g/mol.

According to another one of the invention embodiments, the average molecular weight of the non-cellulosic polysaccharide derivative of the invention is comprised between about 1,100,000 g/mol and about 3,000,000 g/mol.

According to anyone of the invention embodiments, a composition of the invention comprises from 0.01 to 2 pbw of a non-cellulosic polysaccharide derivative of the invention relative to the total weight of the composition.

A composition of the invention may also comprise mixtures of two or more different non-cellulosic polysaccharide derivative, provided that at least one of these non-cellulosic polysaccharide derivatives is a non-cellulosic polysaccharide derivative of the invention.

In one embodiment, the subject of the invention is a hair care composition for mending split ends comprising at least one non-cellulosic polysaccharide derivative as defined previously, and being devoid of any other ingredient acting as split end mending agent.

In other words, in one embodiment, a hair care composition for mending split ends of the invention comprises, as the sole agent for mending split ends, a non-cellulosic polysaccharide derivative as defined previously and contains no (0 pbw) other ingredient for that purpose.

Advantageously the specific non-cellulosic polysaccharide derivative of the invention may be combined with a wide range of other hair benefit agents, including charged hair benefit agents. It is therefore possible to prepare hair care compositions for mending split ends including stable combinations of the specific non-cellulosic polysaccharide derivative of the invention with other hair care ingredients that provide additional desirable properties.

Advantageously the specific non-cellulosic polysaccharide derivative of the invention may be formulated in rinse-off or in leave-on hair care compositions. The performances in split end mending are satisfactory in both formulations.

According to anyone of the invention embodiments, the hair care composition comprising a non-cellulosic polysaccharide derivative of the invention may be formulated as rinse-off or leave-on type of products.

As used herein, the expression "rinse-off compositions" means compositions which are rinsed off from the hair after application. Reversely the expression "leave-on compositions" means compositions which are not rinsed off from the hair after application.

The non-limiting examples of rinse-off products include shampoos, conditioners, hair straighteners, permanent waves, and hair colors (encompassing permanent, semi-permanent, and temporary hair colors).

Leave-on type of hair care products include but not limited to the following representative examples such as setting lotions, serums, hair sprays, mousses, hair lacquers, hair gels, hair waxes, styling creams, pomades, and tonics. Mention is made that the term "hair spray," as used herein, refers to hair care products that are delivered in any atomized (spray) format, whether they be pressurized or unpressurized.

It is also considered to employ non-cellulosic polysaccharide derivative of the invention in the following non-limiting type of hair care and/or hair styling based end-user formulations such as 2 in 1 shampoos, leave-on and rinse-off conditioners, hair perming products, hair relaxants, permanent hair dyeing systems, hair styling mousses, semi-permanent hair dyeing systems, temporary hair dyeing systems, hair bleaching agents, permanent hair wave systems, hair setting formulations, non-coloring hair preparations, hair-frizz-control gels, hair leave-in conditioners, hair de-tangling products, hair fixatives, hair conditioning mists, hair care pump sprays and other non-aerosol sprays, hair cuticle coats.

The improved split ends mending achieved when using the specific non-cellulosic polysaccharide derivative according to the invention can be emphasized on communication tools used by suppliers of chemical ingredients of hair care compositions, for example on animations or movies, presentations, leaflets, flyers, posters, technical data sheets, formularies, on any support, including on papers and websites. This can be linked to a complete or semi complete composition, or to a particular ingredient used to prepare a composition. The improved split ends mending achieved when using the specific non-cellulosic polysaccharide derivative according to the invention can as well be emphasized on communication tools used in marketing hair care compositions, for example on commercial claims, labels, documentation linked to the composition, commercials, scientific studies backing commercial claims, on any support, including on papers, labels, websites, films or animation. Examples of commercial claims can include cure of split ends, deep repair of hair, split ends sealing or the like. Films or animation can for example show a hair fiber (or a representation thereof) having split ends and a product (or a representation thereof) approaching to the hair fiber and mending (i.e. repairing) split ends.

EXAMPLES

The invention will now be described in further detail by way of the following non limiting examples, wherein the abbreviations have the usual meaning in the art. Water amount indicated as "q.s." are intended to be "the amount required to complete to 100 pbw".

All ingredients are expressed by weight percent of the whole formulation and as level of active ingredients.

The following serum compositions were prepared.

| | Control Formulation | Formulation 1 | Formulation 2 | Comparative Formulation |
|---|---|---|---|---|
| Cationic guar derivative 1 (a) | — | 1 | — | — |
| Cationic guar derivative 2 (b) | — | — | 1 | — |
| Jaguar C-13S (c) | — | — | — | 1 |
| Ethanol | 10 | 10 | 10 | 10 |
| Glycerin | 1 | 1 | 1 | 1 |
| Panthenol | 0.5 | 0.5 | 0.5 | 0.5 |
| Preservative | <0.5 | <0.5 | <0.5 | <0.5 |
| Water | q.s. | q.s. | q.s. | q.s. |

(a) Guar Hydroxypropyl trimonium chloride having a molecular weight of about 2,000,000 g/mol and having a cationic degree of substitution of about 0.2, available from Rhodia
(b) Guar Hydroxypropyl trimonium chloride having a molecular weight below 1,000,000 g/mol and having a cationic degree of substitution between 0.2 and 0.3, available from Rhodia
(c) Guar Hydroxypropyl trimonium chloride having a cationic degree of substitution of about 0.15

Formulation Procedure

Disperse the cationic guar derivative in water. Add glycerin and panthenol. Adjust pH to 4.5-5. Add the preservative and adjust the pH to 4.7. Add the ethanol and verify the pH (≤5). Add water to qsp 100.

Assessment of the Performances on Hair Tresses

Hair tresses were purchased from Kerling International European Natural Human Hair of the following characteristics: Color 5/0. 19 cm total length, 17 cm of free hair. 2.5 cm width. 4 g weight free hair.

Hair Pre-Treatment Protocol

Wet the tress during 1 min under running water (or soak during 10 min in water if using several hair tresses). Apply on the whole tress 3 ml of a 10 pbw active sodium diethoxylated dodecyl sulfate (SLE2S) solution. Shampoo during 1 min, 30 sec on each side. Rinse during 1 min. Squeeze between index and middle finger. Detangle using middle teeth comb followed by fine teeth comb. Leave overnight in the controlled climate room (RH=50%±10, T=23° C.).

Hair Damaging Protocol to Obtain Split Ends

The repeated grooming apparatus, custom-built, is used. The device consists of 10 compartments and allows 10 hair tresses to be combed simultaneously. The 4 combs per compartment are mounted at 90° angles, allowing one complete revolution to comb the tress 3 times. Collection drawers are located under each tress to collect the broken fragments. All experiments were performed under controlled temperature and humidity conditions, in a climate controlled room (RH=50%±10, T=23° C.).

The pre-treated hair tresses undergo repeated grooming during 7.5 hours at 19 rpm in order to create the split-ends.

Measurement of the Percentage of Split End Repaired

The whole procedure takes place in the controlled climate room (RH=50%±10, T=23° C.).

Use 4 g hair tresses pre-treated and then damaged according to the protocols described above. Pick 10 hair fibers all bearing split ends and glue them together with a scotch tape in order to obtain a 10-fiber kit. Count the split ends under the lighted magnifier. Weight 2 mg of the product (resp.: Formulation 1, Formulation 2 or Comparative Formulation) in a plastic weighting cup with the aid of a 0.5 ml capacity disposable transfer pipette dropper, on high precision balance. Gather the 10 fibers by holding them close to the split ends and soak them in the product to collect the maximum quantity. Spread the product out on the split ends (on the approximately last 1 cm towards the tips) with the finger until product absorption. Smooth the fibers once more and put the 10-fiber kit in the oven during 1 min. If needed smooth once to align the fibers and count the split ends left under the lighted magnifier.

The percent of split end repaired (% of Repair) was calculated as follows:

$$\% \text{ of Repair} = \frac{(\text{Original number of split ends}) - (\text{number of split ends left})}{\text{Original number of split ends}}$$

Results were the following:

| Formulation | Control Formulation | Formulation 1 | Formulation 2 | Comparative Formulation |
|---|---|---|---|---|
| % of Repair (calculation) | 10 | 80 | 82 | 55 |
| % or Repair (trend) | Reference | +++ | +++ | + |

Formulation 1 and Formulation 2, which include a specific non-cellulosic polysaccharide derivative in accordance with the invention, exhibit significantly improved split end mending compared to the Comparative Formulation (which includes a non-cellulosic polysaccharide of the prior art outside the scope of the invention) and compared to the Control Formulation (which contains no ingredient acting specifically as agent for mending split ends).

Similar results were obtained using lower amounts of the specific non-cellulosic polysaccharide derivative in accordance with the invention.

For instance, % of Repair higher than 80 were also achieved using 0.5 pbw, 0.3 pbw, and even 0.15 pbw, of the cationic guar derivative 1 described previously, formulated in the serum composition (i.e. control formulation) described previously.

These examples illustrate that the specific non-cellulosic polysaccharide derivative according to the invention, namely non-cellulosic polysaccharide derivatives containing at least one cationic group, wherein said non-cellulosic polysaccharide derivative has a cationic degree of substitution DScat greater than 0.15, is highly effective in mending split ends.

The invention claimed is:

1. A method for mending split ends of hair comprising contacting the hair with split ends with a composition consisting of:
   1. from 0.01 to 2 parts by weight of guar derivative selected form the group consisting of Guar Hydroxypropyl trimonium chloride having a molecular weight of about 2,000,000 g/mol and having cationic degree of substitution of about 0.2 and Guar Hydroxypropyl trimonium chloride having a molecular weight below 1,000,000 g/mol and having a cationic degree of substitution between 0.2 and 0.3
   2. ethanol
   3. glycerin
   4. panthenol
   5. preservative and
   6. water.

2. The method according to claim 1, wherein the guar derivative is the only agent for mending split ends in the composition.

* * * * *